United States Patent

Muto et al.

[11] 4,448,964
[45] May 15, 1984

[54] 1,4-DIHYDROPYRIDINE DERIVATIVES

[75] Inventors: Kenji Muto, Shizuoka; Minoru Watanabe, Tokyo; Takao Hatta, Machida; Toru Sugaya, Tokyo; Yoshinori Takemoto, Shizuoka; Nobuhiro Nakamizo, Machida, all of Japan

[73] Assignee: Kyowa Hakko Kogyo Co., Ltd., Tokyo, Japan

[21] Appl. No.: 367,995

[22] Filed: Apr. 13, 1982

[30] Foreign Application Priority Data

Apr. 17, 1981 [JP] Japan .................. 56-56937

[51] Int. Cl.³ .......................... C07D 401/12
[52] U.S. Cl. .................... 546/194; 546/222
[58] Field of Search ......................... 546/194

[56] References Cited

U.S. PATENT DOCUMENTS

| | | | |
|---|---|---|---|
| 3,985,758 | 10/1976 | Murakami et al. | 424/266 X |
| 3,996,234 | 12/1976 | Bossert et al. | 424/266 X |
| 4,004,014 | 1/1977 | Meyer et al. | 546/194 X |
| 4,044,141 | 8/1977 | Bossert et al. | 546/194 X |
| 4,145,432 | 3/1979 | Sato | 546/194 X |

*Primary Examiner*—Richard A. Schwartz
*Attorney, Agent, or Firm*—Antonelli, Terry & Wands

[57] ABSTRACT

Compounds having coronary and vasodilator effects, a hypotensive effect, and useful as antianginal drugs and drugs for treating hypertension are represented by the following general formula:

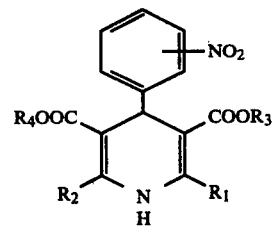

wherein $R_1$ and $R_2$ are the same or different groups and each represents a lower alkyl group, one of $R_3$ and $R_4$ represents a lower alkyl group and the other represents a group of the general formula:

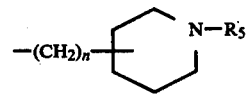

wherein $R_5$ represents an aralkyl group or an acyl group and n represents 0 or an integer of 1–3; the pharmaceutically acceptable acid addition salts thereof are also effective therapeutic compounds.

10 Claims, No Drawings

1,4-DIHYDROPYRIDINE DERIVATIVES

The present invention relates to 1,4-dihydropyridine derivatives and the pharmaceutically acceptable acid addition salts thereof. More particularly, the present invention relates to 1,4-dihydropyridine derivatives or compounds of the general formula (I):

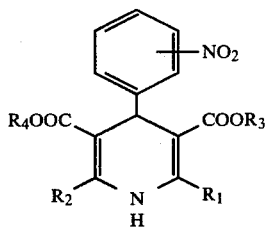

wherein $R_1$ and $R_2$ are the same or different groups and each represents a lower alkyl group, one of $R_3$ and $R_4$ represents a lower alkyl group and the other of $R_3$ and $R_4$ represents the general formula (II):

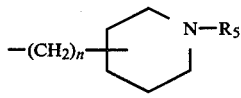

wherein $R_5$ represents an aralkyl group or an acyl group and n represents 0 or an integer of 1–3; and the pharmaceutically acceptable acid addition salts thereof.

The compounds of the present invention are compounds having coronary and peripheral vasodilator effects, a hypotensive effect, etc., and useful as antianginal drugs, drugs for treating hypertension, etc.

Heretofore, among the 1,4-dihydropyridine derivatives, especially 2,6-dimethyl-4-(2-nitrophenyl)-1,4-dihydropyridine-3,5-dicarboxylic acid dimethyl ester (common name: Nifedipine) has been known as the compound having a coronary vasodilator effect, a hypotensive effect, etc.

The present inventors, as the result of screening of novel compounds having a hypotensive effect, have found that the novel 1,4-dihydropyridine compound of the general formula (I) and the pharmaceutically acceptable acid addition salts thereof have an excellent hypotensive effect which is long lasting, and thus have accomplished the present invention.

The present invention is now described in detail hereinbelow.

In the definition of $R_1$, $R_2$, $R_3$ and $R_4$ in the general formula (I), the term "lower alkyl group" represents a methyl group, an ethyl group, an n-propyl group, an isopropyl group, an n-butyl group, an iso-butyl group, a sec-butyl group, a tert-butyl group or a pentyl group.

In the definition of $R_5$ in the general formula (II), the term "aralkyl group" represents a benzyl group or a phenethyl group; and the term "acyl group" represents an acetyl group or a benzoyl group.

As suitable examples of the salts of 1,4-dihydropyridine derivatives of the general formula (I), there may be mentioned inorganic acid salts such as hydrochloride, hydrobromide, phosphate, sulfate, etc. and organic acid salts such as formate, acetate, fumarate, maleate, malate, aspartate, glutamate, etc.

Representative processes for production of the compounds of the present invention are illustrated below.

Process No. 1

(A process according to the procedure described in H. Herbert Fox, et al., J. Org. Chem. 16, 1259 (1951))

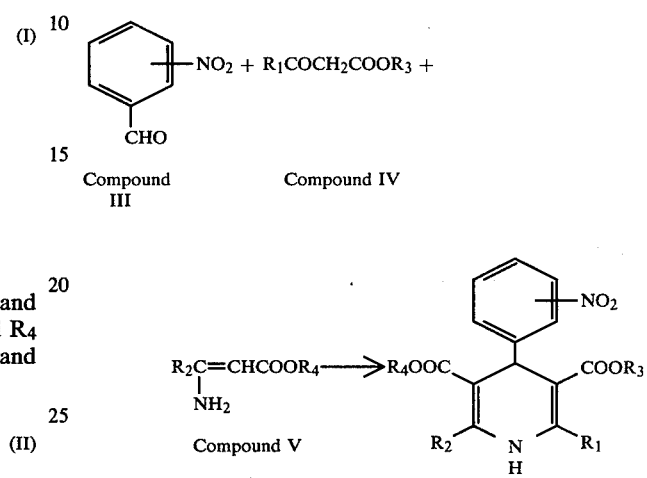

wherein $R_1$, $R_2$, $R_3$ and $R_4$ have the same meaning as defined above.

The details of Process No. 1 are as follows:

The mixing molar ratio of the starting materials. Compounds III, IV and V, is in the range of 1.0:0.8:0.8–1.0:4.0:4.0, preferably 1.0:0.9:0.9–1.0:1.5:1.5.

The reaction is carried out in the presence or absence of an alcohol such as methanol, ethanol, isopropanol, etc., an aromatic hydrocarbon such as benzene, toluene, etc., a halogenated hydrocarbon such as chloroform, carbon tetrachloride, etc., an ether such as tetrahydrofuran, dioxane, etc., an aprotic polar solvent such as acetonitrile, dimethylformamide, etc., water or the like, at room temperature to 150° C., preferably at 30°–100° C. Separation of the desired product from the reaction mixture is effected by conventional operations such as concentration, extraction, column chromatography, recrystallization, etc.

Further, Process Nos. 2–5 are illustrated by the following reaction equations:

Process No. 2

(A process according to the procedure described in B. Loev, et al, J. Medicinal Chem., 17, 956 (1974))

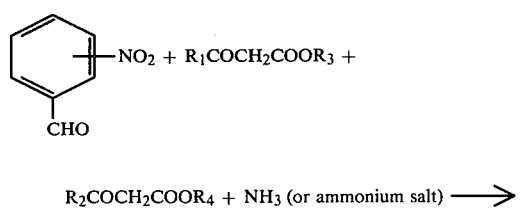

$R_2COCH_2COOR_4 + NH_3$ (or ammonium salt) $\longrightarrow$

-continued

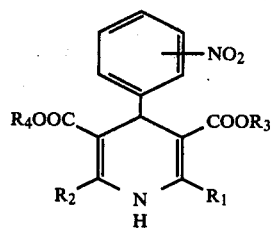

Process No. 3

(A process according to the procedure described in M. Iwanami, et al, Chem. Pharm. Bull., 27, 1426 (1979))

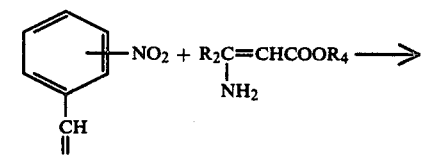

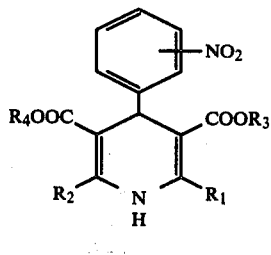

Process No. 4

(A process according to the procedure described in M. Iwanami, et al, Chem. Pharm. Bull., 27, 1426 (1979))

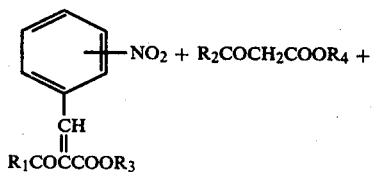

-continued

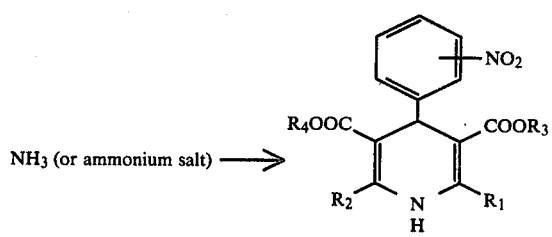

Process No. 5

(A process according to the procedure described in T. Shibanuma, et al, Chem. Pharm. Bull., 28, 2809 (1980))

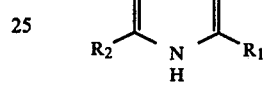

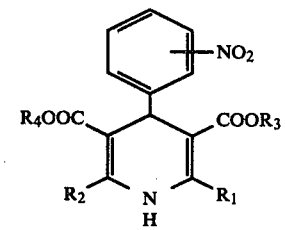

wherein $R_1$, $R_2$, $R_3$ and $R_4$ have the same meaning as defined above.

The hypotensive effect of representative compounds of the present invention is shown below.

Hypotensive Effect

To spontaneous hypertensive rats (SHR) is administered orally a suspension of the test compound in a 0.5% CMC physiological saline, and the systolic pressure of the tail artery is measured on an auto hemodinatometric recorder (Ueda Seisaku-sho). The results are given in Table 1, wherein the compounds of Examples 1, 2 and 4, which are described hereinafter, and two reference compounds are compared.

TABLE 1

| Test Compound | Dose mg/kg | No. of Animals | Pressure before Administration (mmHg) | Change in Pressure (Pressure before administration - Pressure after Administration mmHg) | | | | | | |
|---|---|---|---|---|---|---|---|---|---|---|
| | | | | 10 min | 30 min | 1 hr | 2 hr | 3 hr | 4 hr | 5 hr |
| Compound of Ex. 1 | 3 | 5 | 183 ±8.8 | 44 ±6.3 | 45 ±6.3 | 28 ±8.1 | 37 ±9.4 | 31 ±10.6 | 30 ±9.1 | 23 ±8.8 |
| Compound of Ex. 2 | 3 | 4 | 214 ±10.1 | 67 ±7.8 | 65 ±4.0 | 69 ±12.5 | 45 ±2.9 | 38 ±1.5 | 31 ±4.4 | 27 ±3.8 |
| Compound of Ex. 4 | 3 | 4 | 208 ±9.0 | 67 ±17.2 | 88 ±21.1 | 102 ±12.5 | 111 ±7.4 | 84 ±15.4 | 80 ±10.8 | 64 ±9.0 |
| Comparative Drug A | 3 | 4 | 181 ±10.6 | 39 ±11.9 | 16 ±9.4 | 3 ±10.6 | 18 ±8.9 | −2 ±6.8 | 3 ±5.1 | 9 ±6.3 |
| Compara- | 3 | 4 | 187 | 41 | 26 | 12 | 18 | 22 | 9 | 12 |

TABLE 1-continued

| | | | Hypotensive Effect (Oral Administration) | | | | | | | |
|---|---|---|---|---|---|---|---|---|---|---|
| | | | Pressure before Administration (mmHg) | Change in Pressure (Pressure before administration - Pressure after Administration mmHg) | | | | | | |
| Test Compound | Dose mg/kg | No. of Animals | | 10 min | 30 min | 1 hr | 2 hr | 3 hr | 4 hr | 5 hr |
| tive Drug B | | | ±5.6 | ±8.1 | ±15.0 | ±14.5 | ±5.6 | ±8.8 | ±7.5 | ±5.7 |

Comparative Drug A: Nifedipine
Comparative Drug B: 2,6-Dimethyl-4-(3-nitrophenyl)-1,4-dihydropyridine-3,5-dicarboxylic acid-3-methyl ester-5-β-(N—benzyl-N—methylamino)ethyl ester hydrochloride [Compound of U.S. Pat. No. 3,985,758; Japanese Patent Publication 6417/1981]

From Table 1, it is obvious that the compounds of the present invention have a superior and long-lasting hypotensive effect as compared with Comparative Drugs A and B.

The present invention is more particularly described by the following examples and reference examples.

EXAMPLE 1

In this example, 2.49 g of m-nitrobenzaldehyde, 1.90 g of methyl β-aminocrotonate and 5.0 g of acetoacetic acid-N-benzyl-4-piperidinyl ester obtained in Reference Example 1 (hereinafter described) were added to 7 ml of tetrahydrofuran (hereinafter referred to as THF), and stirring was effected at reflux for 28 hours. The reaction mixture was concentrated under reduced pressure, and the desired product was separated by silica gel column chromatography (eluent:chloroform:methanol=20:1 v/v). The fractions containing the desired product were concentrated, then dissolved in 25 ml of acetone, and acidified by adding ether saturated with hydrogen chloride to obtain yellow crystals. The crystals were filtered out, and dried to obtain 2.14 g of 2,6-dimethyl-4-(3-nitrophenyl)-1,4-dihydropyridine-3,5-dicarboxylic acid-3-(N-benzyl-4-piperidinyl) ester-5-methyl ester hydrochloride [compound of the general formula (I) wherein $R_1=R_2=R_4=CH_3$,

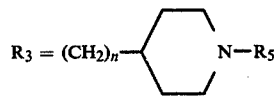

wherein n=0,

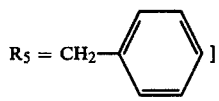

(yield: 23.2%).
m.p.: 249°–252° C.
IR spectrum (KBr, cm$^{-1}$): 1698, 1643, 1525, 1345
NMR spectrum (DMSO-d$_6$,δ): 1.60–2.30(4H, m),2.33(6H, s), 2.70–3.50(4H, m), 3.43(2H, s), 3.60(3H, s), 4.30(1H, m), 5.00(1H, s), 7.30–8.20(9H, m), 9.27(1H, s)
Elemental analysis for C$_{28}$H$_{32}$N$_3$O$_6$Cl:

| | C | H | N |
|---|---|---|---|
| Found (%) | 61.75 | 6.30 | 7.35 |
| Calculated (%) | 62.04 | 5.96 | 7.75 |

EXAMPLE 2

In this example, 3.20 g of m-nitrobenzaldehyde, 2.44 g of methyl β-aminocrotonate and 6.75 g of acetoacetic acid-N-phenethyl-4-piperidinyl ester obtained in Reference Example 2 (hereinafter described) were added to 10 ml of THF, and stirring was effected at reflux for 37 hours. The reaction mixture was concentrated and thereafter the desired product was separated by silica gel column chromatography (eluent:chloroform:methanol=30:1 v/v). The fractions containing the desired product were concentrated and dissolved in 25 ml of acetone and 9 ml of water, and further 5 ml of 4 N hydrochloric acid was added, followed by stirring at room temperature for an hour. Thereafter, the reaction mixture was concentrated and dissolved in 100 ml of chloroform. This was washed with 75 ml portions of water twice, dried on anhydrous sodium sulfate, and then concentrated again. The concentrate was recrystallized from 26 ml of ethanol to obtain 5.20 g of yellow 2,6-dimethyl-4-(3-nitrophenyl)-1,4-dihydropyridine-3,5-dicarboxylic acid-3-(N-phenethyl-4-piperidinyl) ester-5-methyl ester hydrochloride [compound of the general formula (I) wherein $R_1=R_2=R_4=CH_3$,

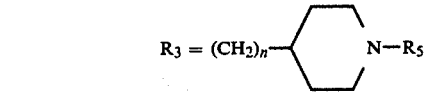

wherein n=0,

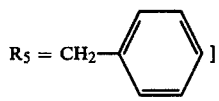

yield: 44.2%)
m.p.: 157°–158° C.
IR spectrum (KBr, cm$^{-1}$): 1694, 1525, 1350
NMR spectrum: (HCl free, CDCl$_3$, δ): 1.50–2.10 (4H, broad), 2.36–2.56(2H, broad), 2.33(3H, s), 2.37(3H,s), 2.56–3.10(6H, broad), 3.67(3H, s), 4.60–5.10(1H, broad), 5.12(1H, s), 6.13(1H, s), 7.20(5H, s), 7.20–8.30 (4H, m)
Elemental analysis for C$_{29}$H$_{34}$N$_3$O$_6$Cl:

| | C | H | N |
|---|---|---|---|
| Found (%) | 62.37 | 6.17 | 7.31 |
| Calculated (%) | 62.63 | 6.18 | 7.56 |

EXAMPLE 3

In this example, 2.74 g of m-nitrobenzaldehyde, 2.09 g of methyl β-aminocrotonate and 5.50 g of acetoacetic acid-N-benzoyl-4-piperidinyl ester obtained in Reference Example 3 (hereinafter described) were added to 10 ml of THF, and stirring was effected at reflux for 33 hours. The reaction mixture was treated similarly as in Example 1 to obtain 2.84 g of 2,6-dimethyl-4-(3-nitrophenyl)-1,4-dihydropyridine-3,5-dicarboxylic acid-3-(N-benzoyl-4-piperidinyl) ester-5-methyl ester [compound of the general formula (I) wherein $R_1=R_2=R_4=CH_3$, $R_3 = (CH_2)_n$—⟨piperidine⟩—$N-R_5$ wherein n=0, $R_5 = \overset{\text{O}}{\underset{\|}{C}}$—⟨phenyl⟩ ]

(yield: 30.2%)
m.p.: 213.5°–216.5° C.
IR spectrum (KBr, cm$^{-1}$): 1690, 1610, 1530 1350
NMR spectrum (CDCl$_3$, δ): 1.30–2.20(4H, broad), 2.28(3H, s), 2.32(3H, s), 3.70(3H, s), 3.10–4.10(4H, broad), 5.15(1H, s) 4.85–5.20(1H, broad), 7.10(1H, s) 7.30–8.10(9H, m)
Elemental analysis for $C_{28}H_{29}N_3O_7$:

|  | C | H | N |
|---|---|---|---|
| Found (%) | 64.43 | 5.75 | 8.00 |
| Calculated (%) | 64.73 | 5.63 | 8.09 |

EXAMPLE 4

In this example, 3.02 g of m-nitrobenzaldehyde, 2.53 g of methyl β-aminocrotonate and 5.5 g of acetoacetic acid-N-benzyl-3-piperidinyl ester obtained in Reference Example 4 (hereinafter described) were added to 10 ml of THF, and stirring was effected at reflux for 19 hours. The reaction mixture was treated similarly as in Example 1 to obtain 2.10 g of yellow 2,6-dimethyl-4-(3-nitrophenyl)-1,4-dihydropyridine-3,5-dicarboxylic acid-3-(N-benzyl-3-piperidinyl) ester-5-methyl ester hydrochloride [compound of the general formula (I) wherein $R_1=R_2=R_4=CH_3$, $R_3 = (CH_2)_n$—⟨piperidine⟩—$N-R_5$ wherein n=0, $R_5 = CH_2$—⟨phenyl⟩ ]

(yield: 19.4%).
m.p.: 176.0°–178.0° C.
IR spectrum (KBr, cm$^{-1}$): 1670–1690, 1525, 1345
NMR spectrum (DMSO-d$_6$, δ):1.33–2.17(4H, broad), 2.33(6H, s), 2.70–3.36(4H, broad), 3.57(3H, s), 4.40(2H, s), 4.98(1H, s), 5.20(1H, s), 7.30–8.20(9H, m), 9.4(1H, broad)
Elemental analysis for $C_{28}H_{32}N_3O_6Cl$:

|  | C | H | N |
|---|---|---|---|
| Found (%) | 61.72 | 6.01 | 7.72 |
| Calculated (%) | 62.04 | 5.96 | 7.75 |

EXAMPLE 5

In this example, 2.50 g of m-nitrobenzaldehyde, 1.90 g of methyl β-aminocrotonate and 5.27 g of acetoacetic acid-N-benzyl-2-piperidinylmethyl ester obtained in Reference Example 5 (hereinafter described) were added to 7 ml of THF, and stirring was effected at reflux for 25 hours. The reaction mixture was treated similarly as in Example 2 to obtain 2.49 g of yellow 2,6-dimethyl-4-(3-nitrophenyl)-1,4-dihydropyridine-3,5-dicarboxylic acid-3-(N-benzyl-2-piperidinylmethyl) ester-5-methyl ester hydrochloride [compound of the general formula (I) wherein $R_1=R_2=R_4=CH_3$, $R_3 = (CH_2)_n$—⟨piperidine with $N-R_5$⟩ wherein n=1, $R_5 = CH_2$—⟨phenyl⟩ ]

(yield: 27.1%).
m.p.: 92°–94° C.
IR spectrum (KBr, cm$^{-}$): 1680, 1527, 1345
NMR spectrum (HCl, free, CDCl$_3$, δ): 1.15–1.80(6H, broad), 1.90–3.00(3H, broad), 2.33(3H, s), 2.37(3H, s), 3.01–4.10(2H, m), 3.66(3H, s), 4.23(2H, d), 5.14, 5.17(1H in total), 6.16(1H, s), 7.25(5H, s), 7.30–8.25(4H, m)
Elemental analysis for $C_{29}H_{34}N_3O_6Cl$:

|  | C | H | N |
|---|---|---|---|
| Found (%) | 62.59 | 6.02 | 7.29 |
| Calculated (%) | 62.63 | 6.18 | 7.56 |

EXAMPLE 6

In this example, 5.00 g of m-nitrobenzaldehyde, 3.81 g of methyl β-aminocrotonate and 10.53 g of acetoacetic acid-(N-benzyl-3-piperidinylmethyl) ester obtained in Reference Example 6 (hereinafter described) were reacted in 15 ml of THF at reflux for 33 hours, and thereafter treated similarly as in Example 2 to obtain 5.38 g of yellow 2,6-dimethyl-4-(3-nitrophenyl)-1,4-dihydropyridine-3,5-dicarboxylic acid-3-(N-benzyl-3-piperidinylmethyl) ester-5-methyl ester hydrochloride [compound of the general formula (I) wherein $R_1=R_2=R_4=CH_3$,

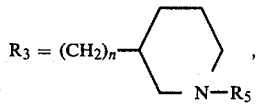

wherein n=1,

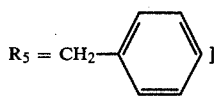

(yield: 29.2%)
m.p.: 218°–220° C.
IR spectrum (KBr, cm$^{-1}$): 1695, 1520, 1340
NMR spectrum (HCl free, CDCl$_3$, δ): 1.33–2.20(5H, broad), 2.32(3H, s), 2.36(3H, s), 2.50–2.93(4H, broad), 3.44(2H, s), 3.67(3H, s), 3.98(2H, d), 5.10(1H, s), 6.01(1H, s), 7.29(5H, s), 7.43–8.23(4H, m)
Elemental analysis for C$_{29}$H$_{34}$N$_3$O$_6$Cl:

|  | C | H | N |
|---|---|---|---|
| Found (%) | 62.48 | 6.05 | 7.49 |
| Calculated (%) | 62.63 | 6.18 | 7.56 |

EXAMPLE 7

In this example, 4.98 g of 2,6-dimethyl-4-(3-nitrophenyl)-1,4-dihydropyridine-3,5-dicarboxylic acid monomethyl ester was suspended in a mixture solvent of 7.5 ml of dimethylformamide and 30 ml of dichloromethane, and 1.2 ml of thionyl chloride was added thereto under ice cooling. The mixture was stirred under ice cooling for 1.5 hours to make a homogeneous solution. 3.39 g of 1-(1-phenylethyl)-4-hydroxypiperidine was added thereto, and then stirring was effected under ice cooling for 2 hours. After completion of the reaction, the reaction mixture was washed with an aqueous sodium bicarbonate, dried over anhydrous sodium sulfate, and the concentrated under reduced pressure. The desired product was separated by silica gel column chromatography (eluent:chloroform:methanol=20:1 v/v). The fractions containing the desired product was treated similarly as in Example 2 to obtain 3.44 g of yellow 2,6-dimethyl-4-(3-nitrophenyl)-1,4-dihydropyridine-3,5-dicarboxylic acid-3-[1-(-phenylethyl)-4-piperidinyl]ester-5-methyl ester hydrochloride (recrystallization solvent: aceton-ethyl acetate) [compound of the general formula (I) wherein R$_1$=R$_2$=R$_4$=CH$_3$,

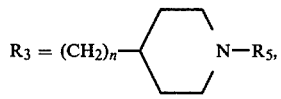

wherein n=0,

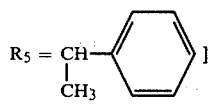

(yield: 41.2%)
m.p.: 180°–184° C.
IR spectrum (KBr, cm$^{-1}$): 1690, 1525, 1350
NMR spectrum (HCl free, CDCl$_3$, δ): 1.32(3H, d), 1.50–1.95(4H, broad), 2.30(6H, s), 2.40–2.90(4H, broad), 3.37(1H, q), 3.62(3H, s), 4.50–4.90(1H, broad), 5.09(1H, s), 6.77(1H, s), 7.23(5H, s), 7.37–8.20(4H, m)
Elemental analysis for C$_{29}$H$_{34}$N$_3$O$_6$Cl:

|  | C | H | N |
|---|---|---|---|
| Found (%) | 62.36 | 6.19 | 7.41 |
| Calculated (%) | 62.64 | 6.16 | 7.56 |

EXAMPLE 8

In this example, 3.02 g of m-nitrobenzaldehyde, 3.18 g of isopropyl β-aminocrotonate and 5.50 g of acetoacetic acid-N-benzyl-4-piperidinyl ester obtained in Reference Example 1 (hereinafter described) were dissolved in 15 ml of iso-propanol, and stirring was effected at reflux for 8 hours. The reaction mixture was treated similarly as in Example 1 to obtain 4.52 g of yellow 2,6-dimethyl-4-(3-nitrophenyl)-1,4-dihydropyridine-3,5-dicarboxylic acid-3-(N-benzyl-4-piperidinyl) ester-5-iso-propyl ester hydrochloride [compound of the general formula (I) wherein R$_1$=R$_2$=CH$_3$, R$_4$=CH(CH$_3$)$_2$,

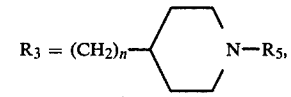

wherein n=0,

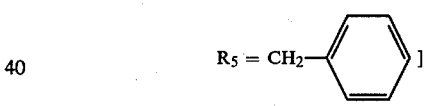

(yield: 39.6%)
m.p.: 211°–214° C.
IR spectrum (Nujol, cm$^{-1}$): 1964, 1527, 1350
NMR spectrum (HCl free, CDCl$_3$, δ): 1.62(6H, dd), 1.53–2.00(4H, broad), 2.00–2.90(10H, m), 3.45(2H, s), 4.50–5.30(2H, m), 5.13(1H, s), 6.67(1H, s), 7.13–8.25(4H, m), 7.27(5H, s)
Elemental analysis for C$_{30}$H$_{36}$N$_3$O$_6$Cl:

|  | C | H | N |
|---|---|---|---|
| Found (%) | 63.20 | 6.37 | 7.37 |
| Calculated (%) | 62.84 | 6.52 | 7.11 |

REFERENCE EXAMPLE 1

To a solution of 10.0 g of 1-benzyl-4-hydroxypiperidine and a catalytic amount of triethylamine in 10 ml of THF was added dropwise 4.62 g of diketene over 15 minutes. After the addition, the reaction was effected at room temperature for 1.5 hours and then at 50°–60° C. for 4.5 hours. The reaction mixture was concentrated, and then distilled under reduced pressure to obtain 7.20 g of acetoacetic acid-N-benzyl-4-piperidinyl ester (yield: 50.0%), b.p. 146° C./0.13 mmHg.
The product crystallizes on cooling.

IRspectrum (KBr, cm$^{-1}$): 1739, 1710

NMR spectrum (CDCl$_3$, δ): 1.40–2.20(4H, m), 2.24(3H, s), 2.30–2.97(4H, m), 3.44(2H, s), 3.51(2H, s), 4.89(1H, m), 7.31(5H, s)

REFERENCE EXAMPLE 2

Similarly as in Reference Example 1, 5.40 g of 1-phenethyl-4-hydroxypiperidine and 2.65 g of diketene were reacted. The reaction mixture was concentrated, and then purified by silica gel column chromatography (eluent:chloroform:methanol=9:1 v/v), to obtain 6.95 g of acetoacetic acid-N-phenethyl-4-piperidinyl ester (yield: 91.3%).

This was used in the reaction of Example 1 without distillation.

IR spectrum (liquid film, cm$^{-1}$): 1735, 1710

NMR spectrum (CCl$_4$, δ): 1.60–3.10(12H, m), 2.30(3H, s), 3.43(2H, s), 4.67–5.10(1H, m), 7.22(5H, s)

The 1-phenethyl-4-hydroxypiperidine was synthesized according to Chem. Abstr. 57, 13741 i.

REFERENCE EXAMPLE 3

In this reference example, 7.03 g of benzoyl chloride was added dropwise to a mixture of 5.05 g of 4-hydroxypiperidine, 6.36 g of sodium carbonate and 60 ml of water at 10° C. with stirring. After the addition, the mixture was maintained at 5° C. for 2 hours. The reaction mixture was filtered, and then filtrate was extracted with dichloromethane. The extract was concentrated, and ether was added to crystallize, whereby 9.20 g of 1-benzoyl-4-hydroxypiperidine was obtained (yield: 90.1%).

m.p.: 91.5°–92.0° C.

IR spectrum (KBr, cm$^{-1}$): 3330, 1600

NMR spectrum (CDCl$_3$, δ): 1.30–2.00(4H, broad), 2.95–4.10(6H, broad), 7.35(5H, s)

Then, 8.16 g of the 1-benzoyl-4-hydroxypiperidine and 3.53 g of diketene were reacted similarly as in Reference Example 1, and the reaction mixture was concentrated to obtain 12.0 g of almost pure oily acetoacetic acid-N-benzoyl-4-piperidinyl ester on thin layer chromatography. This was used directly in the reaction of Example 3.

IR spectrum (liquid film, cm$^{-1}$): 1730, 1710, 1630

NMR spectrum (CCl$_4$, δ): 1.70–2.00(4H, broad), 2.20(3H, s), 3.40(2H, s), 3.20–4.00(4H, broad), 4.90–5.20(1H, broad), 7.30(5H, s)

REFERENCE EXAMPLE 4

A mixture of 15.0 g of 3-hydroxypiperidine hydrochloride, 13.8 g of benzyl chloride, 22.1 g of triethylamine and 120 ml of toluene was stirred at reflux for 4 hours. The reaction mixture was filtered, and the filtrate was concentrated and distilled under reduced pressure to obtain 11.8 g of 1-benzyl-3-hydroxypiperidine (yield: 56.9%). b.p.: 125°–126° C./3.5 mmHg NMR spectrum (CCl$_4$, δ): 1.30–1.90(4H, broad), 2.20–2.50(4H, broad), 3.45(2H, s), 3.40–3.90(1H, broad), 7.20(5H, s)

Then, 11.8 g of the 1-benzyl-3-hydroxypiperidine and 5.6 g of diketene were reacted similarly as in Reference Example 1, and the reaction product was purified by silica gel column chromatography (eluent:chloroform:methanol=9:1 v/v), to obtain 10.65 g of acetoacetic acid-N-benzyl-3-piperidinyl ester (yield: 62.5%). This was used in the reaction of Example 4 without distillation.

NMR spectrum (CDCl$_3$, δ): 1.30–1.90(4H, broad), 2.10–2.95(4H, broad), 2.27(3H, s), 3.43(2H, s), 3.54(2H, s), 4.73–5.2(1H, broad), 7.30(5H, s)

REFERENCE EXAMPLE 5

A mixture of 12.9 g of 2-piperidine methanol, 13.2 g of benzyl chloride, 10.5 g of triethylamine and 50 ml of toluene was stirred at reflux for 4 hours. The reaction mixture was filtered, the filtrate was concentrated, and the concentrate was distilled under reduced pressure to obtain 11.3 g of 1-benzyl-2-piperidine methanol (yield: 52.9%). b.p.: 107° C./2 mmHg IR spectrum (liquid film, cm$^{-1}$): 3375

NMR spectrum (CDCl$_3$, δ): 1.20–1.90(6H, broad), 1.90–2.60(3H, broad), 3.20–4.18(4H, m), 7.27(5H, s)

Then, 10.0 g of the 1-benzyl-2-piperidine methanol and 4.30 g of diketene were reacted similarly as in Reference Example 1, and the reaction product was purified by silica gel column chromatography (eluent:chloroform:methanol=9:1 v/v), to obtain 9.86 g of acetoacetic acid-N-benzyl-2-piperidinylmethyl ester (yield: 69.9%). This was used in the reaction of Example 5 without distillation.

IR spectrum (liquid film, cm$^{-1}$): 1739, 1710

NMR spectrum (CD$_3$OD, δ): 1.20–1.90(6H, broad), 2.25(3H, s), 2.40–3.00(3H, broad), 3.68(2H, dd, J=14 Hz), 4.35(2H, d), 4.57(2H, s), 7.30(5H, s)

REFERENCE EXAMPLE 6

In this reference example, 15.01 g of 1-benzyl-3-piperidine methanol and 6.76 g of diketene were reacted similarly as in Reference Example 1, and the reaction product was purified by silica gel column chromatography (eluent:n-hexane:ethyl acetate=1:1 v/v), to obtain 17.50 g of acetoacetic acid-(N-benzyl-3-piperidinylmethyl) ester (yield: 82.5%).

This was used in the reaction of Example 6 without distillation.

IR spectrum (liquid film, cm$^{-1}$): 1740, 1715

NMR spectrum (CDCl$_3$, δ): 1.33–2.15(5H, broad), 2.23(3H, s), 2.50–2.97(4H, broad), 3.43(2H, s) 3.51(2H, s), 4.07(2H, d), 7.30(5H, s).

What is claimed is:

1. A 1,4-dihydropyridine compound of the formula:

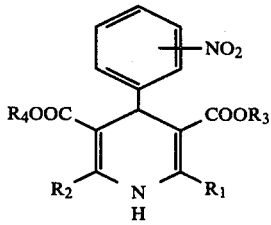

wherein R$_1$ and R$_2$ are the same or different groups and each represents a lower alkyl group, one of R$_3$ and R$_4$ represents a lower alkyl group and the other represents a group of the formula:

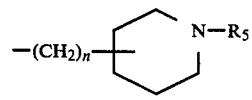

wherein R$_5$ represents a benzyl group, a phenethyl group, an acetyl group or a benzoyl group and n represents 0 or an integer of 1–3; or a pharmaceutically acceptable acid addition salt thereof.

2. The 1,4-dihydropyridine compound of claim 1, wherein the lower alkyl group is a methyl group, an ethyl group, an n-propyl group, an iso-propyl group, an n-butyl group, an iso-butyl group, a sec-butyl group, a tert-butyl group or a pentyl group.

3. 2,6-dimethyl-4-(3-nitrophenyl)-1,4-dihydropyridine-3,5-dicarboxylic acid-3-(N-benzyl-4-piperidinyl)ester-5-methyl ester hydrochloride.

4. 2,6-dimethyl-4-(3-nitrophenyl)-1,4-dihydropyridine-3,5-dicarboxylic acid-3-(N-phenethyl-4-piperidinyl)ester-5-methyl ester hydrochloride.

5. 2,6-dimethyl-4-(3-nitrophenyl)-1,4-dihydropyridine-3,5-dicarboxylic acid-3-(N-benzoyl-4-piperidinyl)ester-5-methyl ester.

6. 2,6-dimethyl-4-(3-nitrophenyl)-1,4-dihydropyridine-3,5-dicarboxylic acid-3-(N-benzyl-3-piperidinyl)ester-5-methyl ester hydrochloride.

7. 2,6-dimethyl-4-(3-nitrophenyl)-1,4-dihydropyridine-3,5-dicarboxylic acid-3-(N-benzyl-2-piperidinylmethyl)ester-5-methyl ester hydrochloride.

8. 2,6-dimethyl-4-(3-nitrophenyl)-1,4-dihydropyridine-3,5-dicarboxylic acid-3-(N-benzyl-3-piperidinylmethyl) ester-5-methyl ester hydrochloride.

9. 2,6-dimethyl-4-(3-nitrophenyl)-1,4-dihydropyridine-3,5-dicarboxylic acid-3-[1-(1-phenylethyl)-4-piperidinyl]-ester-5-methyl ester hydrochloride.

10. 2,6-dimethyl-4-(3-nitrophenyl)-1,4-dihydropyridine-3,5-dicarboxylic acid-3-(N-benzyl-4-piperidinyl)ester-5-iso-propyl ester hydrochloride.

* * * * *